(12) United States Patent
Chou et al.

(10) Patent No.: US 10,060,856 B2
(45) Date of Patent: Aug. 28, 2018

(54) METHOD FOR TEST STRIP RECOGNITION AND INTERPRETATION

(71) Applicant: HTC Corporation, Taoyuan (TW)

(72) Inventors: Fu-Chiang Chou, Taoyuan (TW); Yung-Lung Chang, Taoyuan (TW); Fu-Cheng Fan, Taoyuan (TW); Yi-Chi Lin, Taoyuan (TW); Chin-Hua Hsieh, Taoyuan (TW); Wei-Cheng Hsu, Taoyuan (TW); Syuan-He Shih, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 15/708,154

(22) Filed: Sep. 19, 2017

(65) Prior Publication Data
US 2018/0003645 A1    Jan. 4, 2018

Related U.S. Application Data

(62) Division of application No. 15/054,146, filed on Feb. 26, 2016, now Pat. No. 9,810,639.
(Continued)

(51) Int. Cl.
*G01J 3/46*    (2006.01)
*G01N 21/84*   (2006.01)
(Continued)

(52) U.S. Cl.
CPC ........ *G01N 21/8483* (2013.01); *A61B 5/0077* (2013.01); *A61B 5/01* (2013.01);
(Continued)

(58) Field of Classification Search
CPC .... G01N 21/8483; A61B 5/0077; A61B 5/01; A61B 5/021; A61B 5/0402; A61B 2562/0295; A61B 2562/242
(Continued)

(56) References Cited

U.S. PATENT DOCUMENTS 5,782,757 A * 7/1998 Diab .................. A61B 5/02427
356/41
9,568,432 B2 * 2/2017 Baxi .................... G01N 21/251
(Continued)

FOREIGN PATENT DOCUMENTS

CN    102008294    4/2011
CN    104198482    12/2014
(Continued)

OTHER PUBLICATIONS

"Office Action of China Counterpart Application", dated Jun. 5, 2018, p1-p11.

*Primary Examiner* — Hina F Ayub
(74) *Attorney, Agent, or Firm* — JCIPRNET (57) ABSTRACT

A method for test strip recognition and interpretation is provided. The method includes the following steps. A plurality of test strips are provided, wherein the test strips are configured to examine a plurality of physiologic parameters respectively, and the test strips respectively have a plurality of color characteristics corresponding to the physiologic parameters respectively. A plurality of physiologic parameter examinations are performed to the corresponding test strips respectively, so as to obtain a plurality of test reactions. An image of the test strips is captured. The color characteristics and the test reactions of the test strips are obtained according to the image. The physiologic parameters examined by the test strips respectively are obtained according to the color characteristics. The physiologic parameters examined by the test strips are matched with the test reactions to obtain a plurality of physiologic parameter examination results.

7 Claims, 6 Drawing Sheets

Related U.S. Application Data (60) Provisional application No. 62/156,855, filed on May 4, 2015.

(51) Int. Cl.
    *A61B 5/00*           (2006.01)
    *A61B 5/0402*       (2006.01)
    *A61B 5/021*        (2006.01)
    *A61B 5/01*         (2006.01)

(52) U.S. Cl.
    CPC .............. *A61B 5/021* (2013.01); *A61B 5/0402* (2013.01); *A61B 2562/0295* (2013.01); *A61B 2562/242* (2013.01)

(58) Field of Classification Search
    USPC .................................................. 356/73, 402
    See application file for complete search history.

(56) References Cited

U.S. PATENT DOCUMENTS

| | | | |
|---|---|---|---|
| 2011/0282173 A1* | 11/2011 | Fonduca | A61B 5/14532 600/365 |
| 2014/0099237 A1* | 4/2014 | Chang | A61B 5/6898 422/82.01 |
| 2016/0139156 A1* | 5/2016 | Lakdawala | G01N 21/8483 435/7.92 |

FOREIGN PATENT DOCUMENTS

| | | |
|---|---|---|
| CN | 104215628 | 12/2014 |
| CN | 104318584 | 1/2015 |
| CN | 104568932 | 4/2015 |

\* cited by examiner

METHOD FOR TEST STRIP RECOGNITION AND INTERPRETATION

CROSS-REFERENCE TO RELATED APPLICATION

This is a divisional application of patent application Ser. No. 15/054,146, filed on Feb. 26, 2016, which claims the priority benefits of U.S. provisional application Ser. No. 62/156,855, filed on May 4, 2015. The entirety of each of the above-mentioned patent applications is hereby incorporated by reference herein and made a part of this specification.

BACKGROUND OF THE INVENTION

Field of the Invention

The present invention generally relates to an examination system and a method for recognition and interpretation. More particularly, the present invention relates to a system for physiologic parameter examination and a method for test strip recognition and interpretation.

Description of Related Art

In recent years, as material life improves, people have become more conscious concerning the issues of health. Most people are unaware of their current health condition or environmental condition, and overlook warning signals from their body. Thus, in order to let the public be able to observe their own physiological condition, various measuring devices having been gradually emerging. As such, the public can use the various measuring devices to monitor their own physiological condition, and immediately determine if there are any unusual problems occurred with their health condition. By this manner, the user can pay more attention to their physical condition, and make any suitable adjustments. Therefore, using information technology to collect various physiological signals and analyze physiological heath status of an individual case is a joint collaborative research topic for the fields of medical care and information science.

Most signs of diseases will show slight differences in the variability of operation and rhythm of physical organs, so many international companies and medical researchers have provided processes and methods for monitoring and analyzing the physiological signal. However, all kinds of apparatuses and accessories for physiological signal monitoring and examination on the market nowadays are inconvenient to carry around. Moreover, an additional calculating device installed with at least one examination program is needed to perform sequential analyses and applications. Therefore, conventional apparatuses are usually large in size, hard to operate and expensive. Generally, each of the apparatuses is customized for particular examination or for single purpose, which is still inconvenient for users.

SUMMARY OF THE INVENTION

Accordingly, the present invention is directed to a system for physiologic parameter examination, which is configured to be integrated with a portable electronic device to perform optics and image analyses and calculations to obtain examination results.

The present invention is further directed to a method for test strip recognition and interpretation, which can perform test strip recognition and interpretation through optics and image analyses and calculations.

The present invention provides a system for physiologic parameter examination includes a housing and a test-strip tray. The housing includes a carrying cavity disposed on a top surface of the housing and including a window. The carrying cavity is configured to receive a portable electronic device having an image capturing component. The image capturing component corresponds to the window. The test-strip tray is movably disposed in the housing and located below the carrying cavity. The test-strip tray is configured to carry at least one test strip. The image capturing component is adapted to capture a test reaction of the test strip through the window.

The present invention provides a method for test strip recognition and interpretation. The method includes the following steps. A plurality of test strips are provided, wherein the test strips are configured to examine a plurality of physiologic parameters respectively, and the test strips respectively have a plurality of color characteristics corresponding to the physiologic parameters respectively. A plurality of physiologic parameter examinations are performed to the corresponding test strips respectively, so as to obtain a plurality of test reactions. An image of the test strips is captured. The color characteristics and the test reactions of the test strips are obtained according to the image. The physiologic parameters examined by the test strips respectively are obtained according to the color characteristics. The physiologic parameters examined by the test strips are matched with the test reactions to obtain a plurality of physiologic parameter examination results.

Based on the above-mentioned description, the system for physiologic parameter examination of the invention is configured to be integrated with a portable electronic device, so as to use the image capturing component such as a camcorder of the portable electronic device to capture test reactions of the test strips and perform recognition and calculation by the portable electronic device to obtain and display results of the physiologic parameter examination tested by the test strips. Therefore, the present invention indeed improves the flexibility and convenience of the system for physiologic parameter examination in use.

In addition, the present invention further provides a method for test strip recognition and interpretation, which obtains the color and the test reactions of test strips by capturing the image of the test strips, and recognizes examination items (physiologic parameters to be examined) of the test strips according to the color of the test strips. Then, the physiologic parameters examined by the test strips are matched with the test reactions of the test strips, so as to obtain the examination results of the physiologic parameters. Therefore, the method of the present invention make the test strip recognition and interpretation performed automatically, so as to improve efficiency of the physiologic parameter examination.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Reference will now be made in detail to the present preferred embodiments of the invention, examples of which are illustrated in the accompanying drawings. Wherever possible, the same reference numbers are used in the drawings and the description to refer to the same or like parts.

Figure 1:
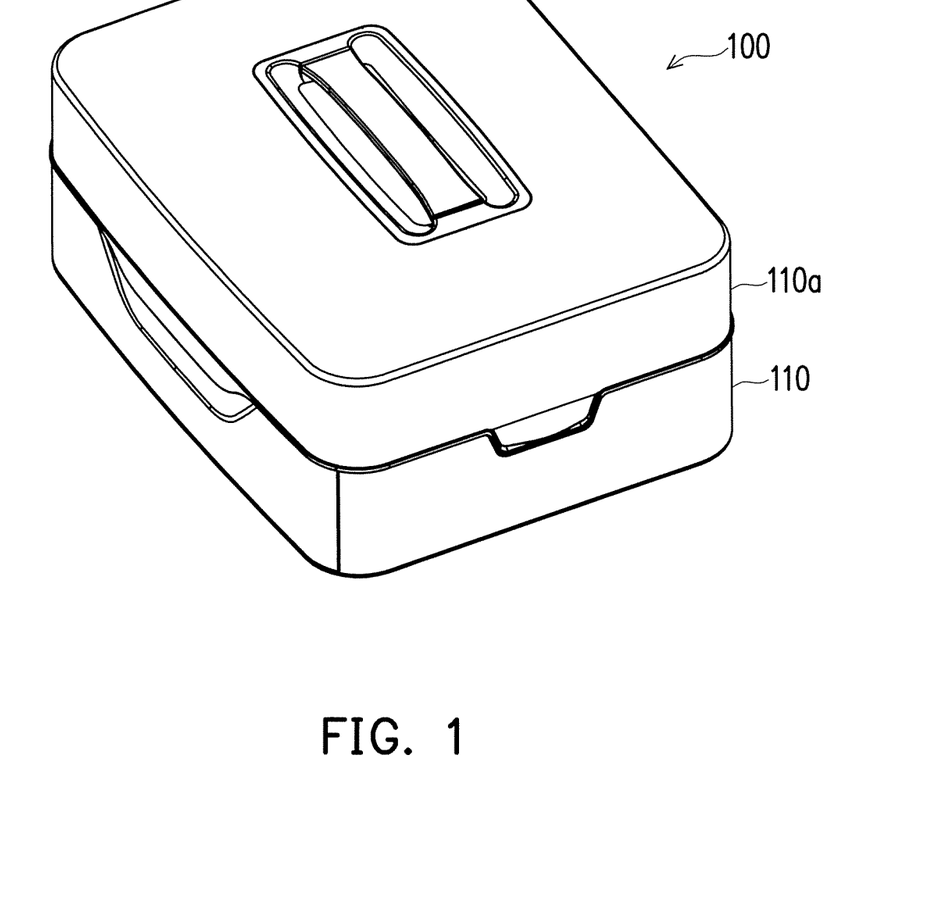
FIG. 1 is a schematic view of a system for physiologic parameter examination according to an embodiment of the present invention.
Figure 2:
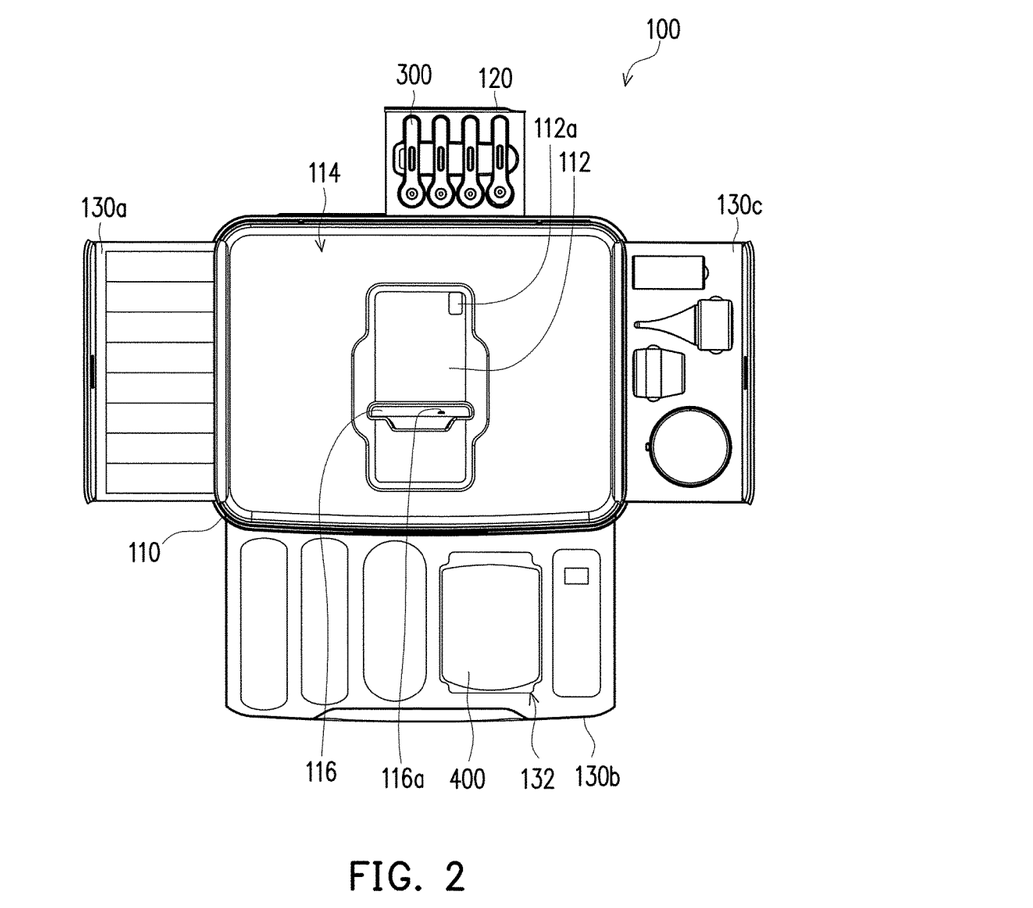
FIG. 2 is a schematic view of inner components of the system for physiologic parameter examination in FIG. 1.
Figure 3:
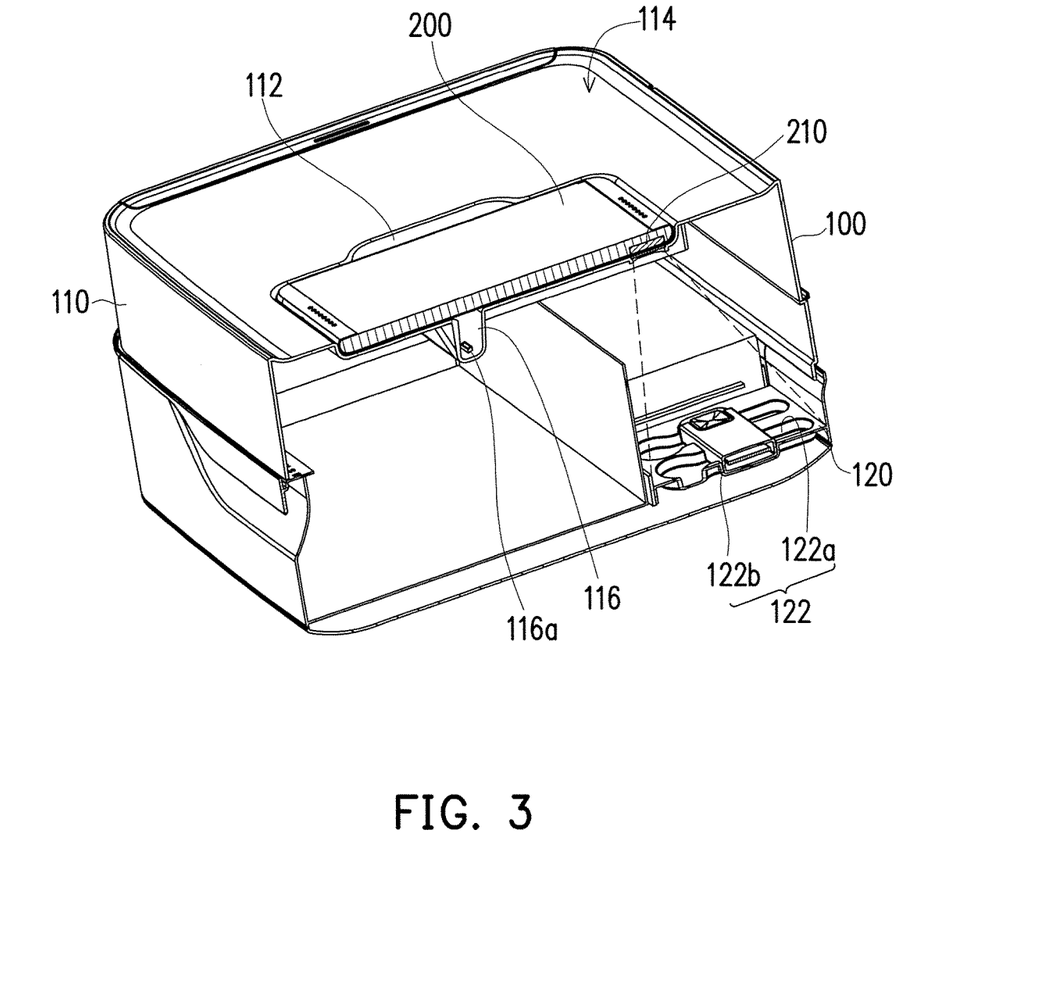
FIG. 3 is cross-sectional view of the system for physiologic parameter examination in FIG. 1.

Referring to FIG. 1 to FIG. 3, in the present embodiment, the system for physiologic parameter examination 100 may include a cover 110a, a housing 110 and a test-strip tray 120. The cover 110a is disposed on the housing 110 to cover a top surface 114 of the housing 110. It should be noted that the structure of the cover 110a is omitted in both FIG. 2 and FIG. 3 to show inner components of the system for physiologic parameter examination 100 more clearly. In the present embodiment, the housing 110 includes a carrying cavity 112 disposed on the top surface 114 of the housing 110, and the carrying cavity 112 includes a window 112a. The carrying cavity 112 is configured to receive a portable electronic device 200 shown in FIG. 3, which has an image capturing component 210, and the location of the image capturing component 210 is corresponding to the window 112a of the carrying cavity 112. In the present embodiment, the image capturing component 210 can be a camcorder, and the camcorder is illustrated hereinafter, but the present invention is not limited thereto. In the present embodiment, the portable electronic device 200 may be, for example, a smart phone with image capturing function. Certainly, the present invention is not limited thereto. In other embodiment, the portable electronic device 200 may also be a tablet PC or other portable electronic device having image capturing component. Any kinds of the above-mentioned portable electronic devices may have the function of interne connection and are capable of performing data transmission with a particular destination. Therefore, the portable electronic device 200 may also have a wireless transmission module to perform data transmission with the particular destination through wireless network.

In the present embodiment, the test strip tray 120 is movably disposed in the housing 110 and located below the carrying cavity 112. For instance, the test strip tray 120 may be a drawer structure, which can move along, for example, a sliding rail between a closed position as shown in FIG. 1 and an open position as shown in FIG. 2. The test strip tray 120 is configured to carry at least one test strip 300. When the test strip tray 120 is located in the open position, at least a part of the test-strip tray 120 is exposed, so a user may put the test strips 300 onto the test strip tray 120 or pick up the test strips 300 from the test-strip tray 120. When the test-strip tray 120 is located in the closed position, the test-strip tray 120 is located in the housing 110 to jointly form a closed space with the housing 110. A shooting range of the image capturing component 210 (illustrated in dotted line in FIG. 3) is corresponding to the position of the test-strip tray 120. The image capturing component 210 is configured to capture an image of the test reactions of the test strips 300 on the test strip tray 120 through the window 112a.

To be more specific, an inner wall of the test strip tray 120 may be a light-absorbing surface to prevent the inner wall of the test strip tray 120 from reflecting light and affects the capturing result of the image capturing component 210. Specifically, the inner wall of the test strip tray 120 may be a black surface or the inner wall of the test strip tray 120 may be coated with light absorbing coating. Moreover, when the test strip tray 120 is located in the closed position, the test strip tray 120 and the housing 110 jointly form a closed space to prevent external light from leaking in, so as to improve image quality captured by the image capturing component 210.

With such structural disposition, the system for physiologic parameter examination 100 of the present embodiment can be integrated with the portable electronic device 200, so as to use the image capturing component 210 of the portable electronic device 200 to capture the image of the test reactions of the test strips and perform recognition and calculation by the portable electronic device 200 to obtain and display preliminary results of the physiologic parameter examination tested by the test strips 300. If further analyses are needed, the examination results may be transmitted to a particular destination through internet by the portable electronic device 200. The particular destination may be, for example, a cloud system, a data storing and analyzing system or a data base of a hospital, medical survey or research organization, or health examination center, etc., so as to obtain an advanced examination result and suggestion. Furthermore, when the system for physiologic parameter examination 100 is electrically connected to the portable electronic device 200, the system for physiologic parameter examination 100 may also perform data transmission with the portable electronic device 200 to obtain the preliminary examination result or the advanced examination result.

In detail, in the present embodiment, the number of the test strips 300 is plural, and is configured to examining a plurality of physiologic parameters respectively. For example, the test strips 300 may include all kinds of blood test strips, urine test strips, breath test strips, blood sugar test strips, etc. Moreover, the colors of the test strips 300 are different from each other for examining different physiologic parameters respectively, so as to distinguish different examining purposes. After the image capturing component 210 of the portable electronic device 200 captures the image of the test strips 300, algorithm, such as image analyzing and recognition software, pre-installed in the portable electronic device 200 can be used to analyze the image to recognize the colors of the test strips, so as to obtain the corresponding examining items, such as all kinds of examinations of blood, urine, breath and/or blood sugar, etc., then the results are combined for calculation, so as to obtain the preliminary examination results of the physiologic parameters examined by the test strips.

Figure 4:
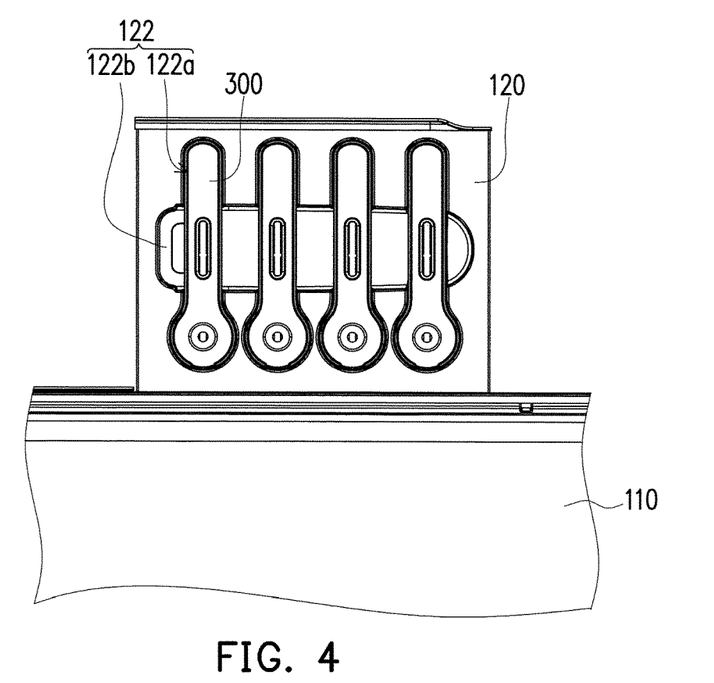
FIG. 4 is schematic view of the test-strip tray of the system for physiologic parameter examination in FIG. 2.

Referring to FIG. 4, in the present embodiment, the test-strip tray 120 may include a plurality of positioning grooves 122 configured to receive and position the test strips 300 respectively. In detail, the positioning grooves 122 may include a plurality of first positioning grooves 122a and a second positioning groove 122b. The first positioning grooves 122a are parallel to each other, and the second positioning groove 122b intersects each of the first positioning grooves 122a. In the present embodiment, the first positioning grooves 122a are parallel to each other, and the second positioning groove 122b perpendicularly intersects each of the first positioning grooves 122a. The first positioning groove 122a is configured to receive all kinds of different blood test strips, and the second positioning groove 122b is configured to receive a urine test strip. Certainly, the disposition in the present embodiment is merely for illustration and the present invention is not limited thereto.

Certainly, the disposition in the present embodiment is merely for illustration and the present invention is not limited thereto.

Figure 5:
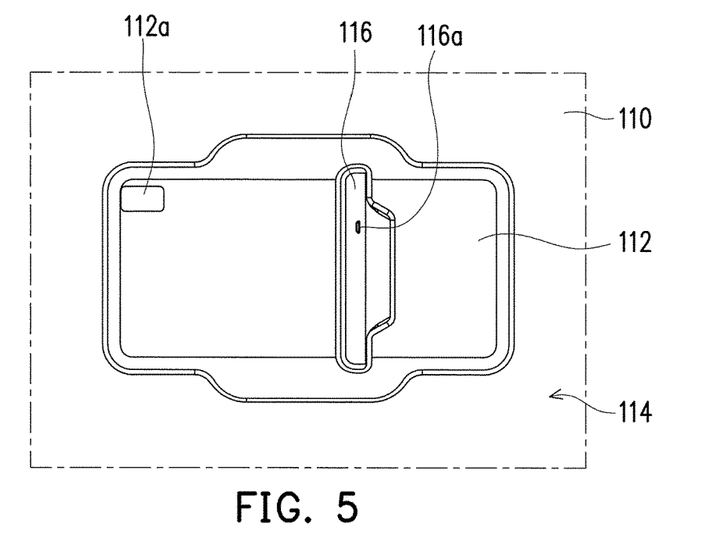
FIG. 5 is a schematic view of the connecting cavity and the carrying cavity of the system for physiologic parameter examination in FIG. 2.
Figure 6:
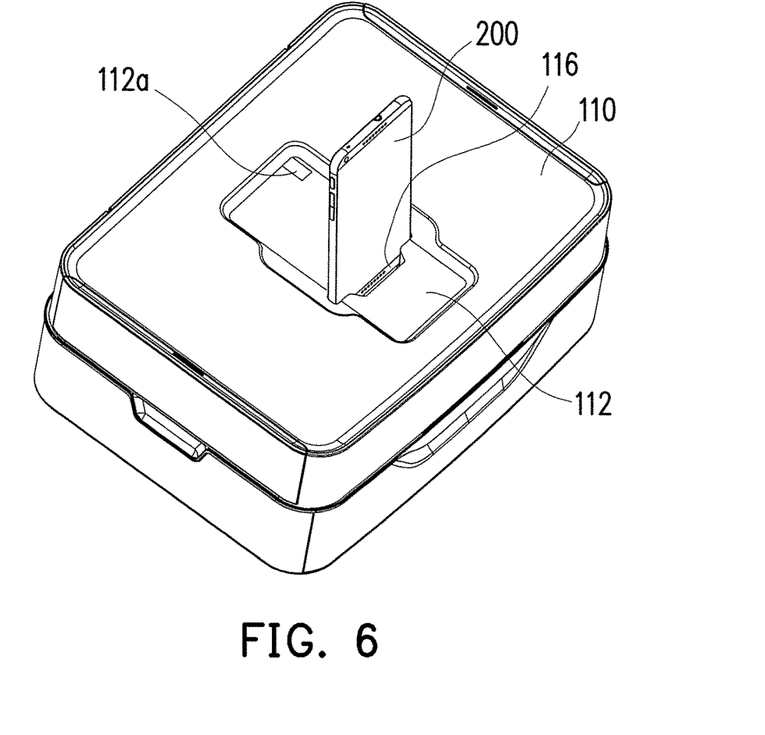
FIG. 6 is a schematic view of a portable electronic device inserted in the connecting cavity of the system for physiologic parameter examination in FIG. 3.

Referring to FIG. 5 and FIG. 6, in the present embodiment, the housing 110 as shown in FIG. 5 may further include a connecting cavity 116 disposed on the stop surface 114 of the housing 110. Moreover, the connecting cavity 116 includes an electrical connector 116a. As such, a bottom portion of the portable electronic device 200 can be inserted into the connecting cavity 116 in portrait mode shown in FIG. 6, so as to be electrically connected to the electrical connector 116a, such that the portable electronic device 200 can be charged by the electrical connector 116a, and perform data transmitting with the system for physiologic parameter examination 100 through the electrical connector 116a. In the present embodiment, the connecting cavity 116 is located in the carrying cavity 112. Namely, the disposition locations of the connecting cavity 116 and the carrying cavity 112 can be overlapped with each other. Certainly, the present embodiment is merely for illustration, the present invention does not limit the disposition locations of the connecting cavity 116.

In addition, the system for physiologic parameter examination 100 of the present embodiment may further include a plurality of device trays 130 as shown in FIG. 2 (the device trays 130a, 130b, 130c illustrated in FIG. 3). Moreover, each of the device trays 130 may include a plurality of containing cavities 132 to contain a plurality of physiologic parameter detecting devices 400 for a user to perform all kinds of different physiologic parameter examinations easily. The physiologic parameter detecting devices 400 may include a camera module, a lens, a test strip set, an electrocardiograph, a blood pressure monitor, a body temperature sensor or any combination thereof.

For example, one of the device trays 130a, 130b, 130c (taking the device tray 130a extended toward left as shown in FIG. 2 for example) may receive a plurality of test strip sets for blood test, urine test, breath test, blood sugar test, etc., respectively. The tested test strip 300 is disposed back to the test strip tray 120 to capture the test reactions by the portable electronic device 200. Another one of the device trays 130a, 130b, 130c (taking the device tray 130b extended downward as shown in FIG. 2 for example) may receive the physiologic parameter detecting devices 400 for examining electrocardiography, oxygen saturation (SpO2), and/or body temperature, etc., and auxiliary devices such as blood pressure monitor, ear thermometer, etc. In the present embodiment, the blood pressure monitor and ear thermometer may be used to provide data such actual blood pressure and body temperature of the user for data correction of the physiologic parameter detecting devices. Yet another one of the device trays 130a, 130b, 130c (taking the device tray 130c extended toward right as shown in FIG. 2 for example) may receive a camera module, a first lens and a second lens, wherein the first lens can be assembled to the camera module to form a device similar to a dermoscopy for the purposes of examining skin lesions such as melanoma. The second lens may also be assembled to the camera module to form a device similar to otoscope for the purpose of examining ear diseases such as otitis media. Certainly, the disposition is merely for illustration. The present invention does not limit the number of the device trays 130 and types and numbers of the physiologic parameter detecting devices contained in the device trays 130.

Figure 7:
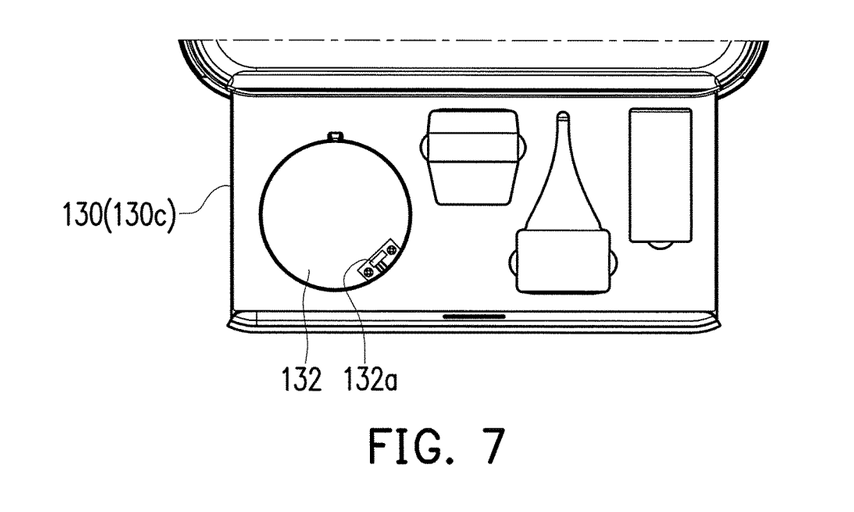
FIG. 7 is a schematic view of the containing cavities of the portable electronic device in FIG. 2.
Figure 8:
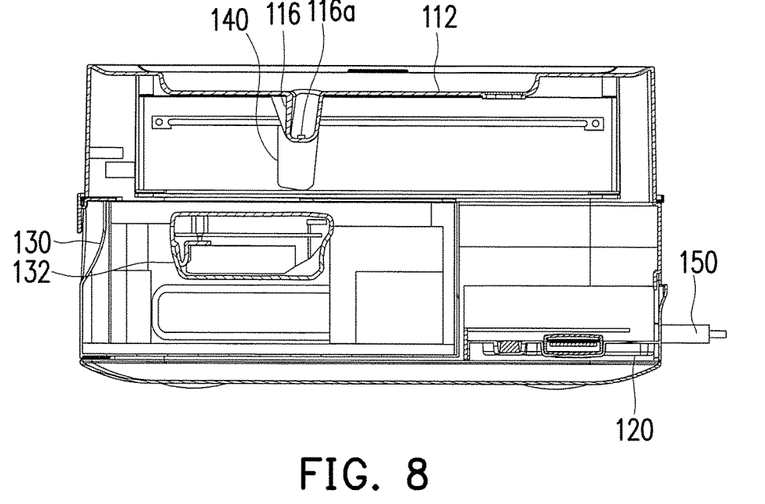
FIG. 8 is another cross-sectional view of the portable electronic device in FIG. 1.

Referring to FIG. 7 and FIG. 8, in the present embodiment, at least one of the containing cavities 132 may include an electrical connector 132a as shown in FIG. 7, and the electrical connector 132a is configured to be electrically connected to the corresponding physiologic parameter detecting device 400 contained in the containing cavities 132, such that the physiologic parameter detecting device 400 can be charged by the electrical connector 132a, and perform a data transmission with the system for physiologic parameter examination 100 through the electrical connector 132a. In addition, the containing cavity 132 may also contain a back-up battery for the physiologic parameter detecting device 400, and the back-up battery may be charged by the electrical connector 132a when the back-up battery is disposed in the containing cavity 132. In the present embodiment, the system for physiologic parameter examination 100 may further include a socket connector 140 and an extensional wire 150 as shown in FIG. 8. The socket connector 140 can be electrically connected to the electrical connector 116a of the connecting cavity 116 and the electrical connector 132a of the containing cavity 132, such that the system for physiologic parameter examination 100 can be electrically connected to and/or perform data transmission with the portable electronic device 200 and the physiologic parameter detecting device 400 respectively through the electrical connectors 116a and 132a. In addition, the system for physiologic parameter examination 100 can be connected to a power supply through the extensional wire 150 to be charged. Alternatively, the system for physiologic parameter examination 100 can be connected to an external electronic device through the extensional wire 150, so as to perform data transmission with the external electronic device.

Figure 9:
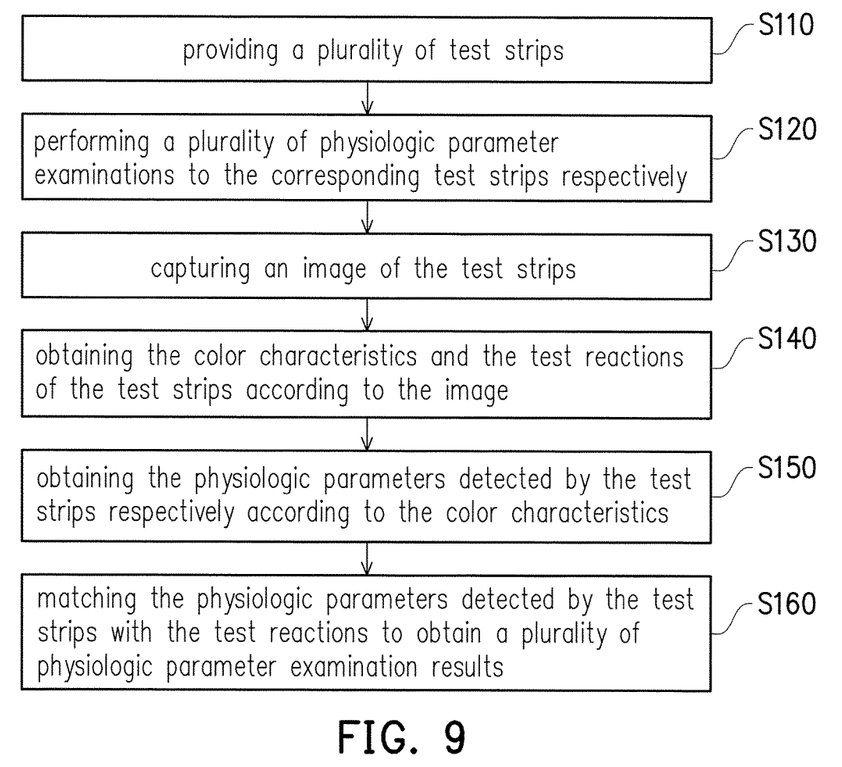
FIG. 9 is a flow chart of a method for test strip recognition and interpretation according to an embodiment of the present invention.

Referring to FIG. 2, FIG. 3 and FIG. 9, the present invention also developed a method for test strip recognition and interpretation, which is applicable to the system for physiologic parameter examination 100 described above. The method for test strip recognition and interpretation includes the following steps. Firstly, step S110 is performed, a plurality of test strips 300 is provided, wherein the test strips 300 can be disposed on the test strip tray 120 of the system for physiologic parameter examination 100 and be configured to examine a plurality of physiologic parameters respectively. The test strips 300 respectively have a plurality of color characteristics corresponding to the physiologic parameters respectively. Namely, the test strips 300 are categorized into different testing purposes, such as all kinds of blood tests, urine tests, breath tests, blood sugar tests, etc., by the color characteristics thereof. Next, step S120 is performed, a plurality of physiologic parameter examinations are performed to the corresponding test strips 300 respectively, so as to obtain a plurality of test reactions. Next, step S130 is performed, an image of the test strips 300 is captured. In the present embodiment, a carrying cavity 112 of the system for physiologic parameter examination 100 is configured to receive and dispose a portable electronic device 200 and the image of the test strip 300 is captured by the portable electronic device 200. Next, step S140 is performed, the color characteristics and the test reactions of the test strips 300 are obtained according to the image. In the present embodiment, the portable electronic device 200 can read and recognize the captured image of the test strip 300 by algorithm, such as image analyzing and recognition software, pre-installed in the portable electronic device 200 to obtain the color characteristics and test reactions (for example, positive reaction, negative reaction, etc.) of the test strips 300. Next, step S150 is performed, the physiologic parameters examined by the test strips 300 respectively are obtained according to the color characteristics of the test strips 300. In the present embodiment, the physiologic parameters to be examined by the test strips 300 are categorized by the colors of the test strips 300, so the portable electronic device 200 can obtain the physiologic parameters examined by the test strips 300 according to the color of the test strips 300. Afterward, step S160 is performed, the physiologic parameters examined by the test strips 300 are matched with the test reactions to obtain a plurality of physiologic parameter examination results. In the present embodiment, the portable electronic device 200 can pair the physiologic parameters examined by the test strips 300 with the test reactions of the test strips 300 to synthetically calculate and obtain the physiologic parameter examination results. As such, the system for physiologic parameter examination 100 can recognize the examination items (physiologic parameters to be examined) of the test strips 300 according to the color of the test strips 300 by the portable electronic device 200, so as to be matched with the test reactions of the corresponding test strips 300 and obtain the physiologic parameter examination results. It should be noted that, the present embodiment does not limit the applicable hardware for the method for test strip recognition and interpretation. Any electronic device having camcorder function and calculation ability can be applied.

In sum, the system for physiologic parameter examination of the invention is configured to be integrated with a portable electronic device, so as to use the image capturing component of the portable electronic device to capture test reactions of the test strips and perform recognition and calculation by the portable electronic device to obtain and display results of the physiologic parameter examination tested by the test strips. Therefore, general users can instantly monitor their body condition at home, so the present invention indeed improves the flexibility and convenience of the system for physiologic parameter examination in use.

In addition, the present invention further provides a method for test strip recognition and interpretation, which obtains the color and the test reactions of test strips by capturing the image of the test strips, and recognizes examination items (physiologic parameters to be examined) of the test strips according to the color of the test strips. Then, the physiologic parameters examined by the test strips are matched with the test reactions of the test strips, so as to obtain the examination results of the physiologic parameters. Therefore, the method of the present invention make the test strip recognition and interpretation performed automatically, so as to improve efficiency of the physiologic parameter examination.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method for test strip recognition and interpretation, comprising:
    providing a plurality of test strips, wherein the test strips are configured to examine a plurality of physiologic parameters respectively, and the test strips respectively have a plurality of color characteristics corresponding to the physiologic parameters respectively;
    performing a plurality of physiologic parameter examinations with the corresponding test strips respectively, so as to obtain a plurality of test reactions;
    capturing an image of the test strips;
    obtaining the color characteristics and the test reactions of the test strips according to the image;
    obtaining the physiologic parameters examined by the test strips respectively according to the color characteristics; and
    matching the physiologic parameters examined by the test strips with the test reactions to obtain a plurality of physiologic parameter examination results.

2. The method for test strip recognition and interpretation as claimed in claim 1, further comprising:
    after performing the physiologic parameter examinations with the corresponding test strips respectively, disposing the test strips on a test-strip tray in a system for physiologic parameter examination.

3. The method for test strip recognition and interpretation as claimed in claim 2, wherein an inner wall of the test-strip tray is a black surface or covered with a light-absorbing coating.

4. The method for test strip recognition and interpretation as claimed in claim 2, wherein the test-strip tray comprises a plurality of positioning grooves configured to receive and position the test strips respectively.

5. The method for test strip recognition and interpretation as claimed in claim 4, wherein the positioning grooves comprise a plurality of first positioning grooves and a second positioning groove, the first positioning grooves are parallel to each other, and the second positioning groove intersects the first positioning grooves.

6. The method for test strip recognition and interpretation as claimed in claim 2, wherein the step of capturing the image of the test strips further comprises:
    capturing the image of the test strips on the test-strip tray by a portable electronic device disposed on the system for physiologic parameter examination.

7. The method for test strip recognition and interpretation as claimed in claim 6, further comprising:
    when the portable electronic device is electrically connected to the system for physiologic parameter examination, the portable electronic device performing a data transmission with the system for physiologic parameter examination.

* * * * *